United States Patent [19]

Andersen et al.

[11] Patent Number: 4,706,670
[45] Date of Patent: Nov. 17, 1987

[54] DILATATION CATHETER

[75] Inventors: Erik Andersen, Roskilde; Gianni Leoni, Greve Str., both of Denmark

[73] Assignee: Meadox Surgimed A/S, Denmark

[21] Appl. No.: 801,715

[22] Filed: Nov. 26, 1985

[51] Int. Cl.⁴ .......................................... A61M 29/02
[52] U.S. Cl. ................................ 128/344; 128/348.1; 604/282
[58] Field of Search ..................... 128/344, 325, 348.1, 128/341; 604/96, 97, 98, 99, 100, 103, 104, 282

[56] References Cited

U.S. PATENT DOCUMENTS

| | | | |
|---|---|---|---|
| 3,924,632 | 12/1975 | Cook | 604/282 |
| 4,024,873 | 5/1977 | Antoshkiw et al. | |
| 4,299,226 | 11/1981 | Banka | 128/344 |
| 4,327,736 | 5/1982 | Inoue | |
| 4,553,959 | 11/1985 | Hickey et al. | 604/282 X |

FOREIGN PATENT DOCUMENTS

| | | |
|---|---|---|
| 186267 | 7/1986 | European Pat. Off. |
| 2513018 | 10/1975 | Fed. Rep. of Germany |
| 1566674 | 5/1980 | United Kingdom |
| 2130093 | 5/1984 | United Kingdom |

Primary Examiner—Michael H. Thaler
Attorney, Agent, or Firm—Blum Kaplan

[57] ABSTRACT

A balloon catheter for use in angioplasty and the like includes a shaft made of an elastomeric tube reinforced with longitudinally inelastic filaments. In the distal balloon portion of the unpressurized shaft, the filaments lie at an angle which is less than a predetermined critical angle. In the adjacent movable portion of the shaft, the filaments lie at an angle which is greater than the critical angle. When the shaft is pressurized, the balloon portion expands in diameter and the balloon portion contracts in diameter until the filaments in each portion lie at the critical angle. At the same time, the length of the movable portion increases so as to offset the reduction in length of the balloon portion.

30 Claims, 11 Drawing Figures

DILATATION CATHETER

BACKGROUND OF THE INVENTION

This invention relates to catheters. More particularly, the invention relates to dilitation catheters which have a shaft having a portion which can be inflated like a balloon. The balloon portion is expanded by supplying fluid under pressure after it is placed at a point in a blood vessel to increase the patency thereof.

The use of balloon catheters for enlarging the diameter of a blood vessel, for example, at a point of stenosis such as is produced by an accumulation of plaque, is a known medical practice. In one such procedure known as percutaneous transluminal coronary angioplasty, a flexible guide wire is first introduced percutaneously into an artery of a patient and is manipulated to arrive at and penetrate the lumen of the occluded portion of a coronary artery while the patient is viewed on an x-ray imaging screen. The guide wire is followed by a guide catheter which is fed along the guide wire to a point in the coronary artery which is just proximal of the occlusion. The dilatation catheter is then sent along the guide wire, within the guide catheter, into the patient's artery and the balloon portion of the catheter is positioned in the occluded portion of the artery.

One dilatation catheter used in this procedure consists of an inner tube, or cannula, which can pass freely along the guide wire. A catheter shaft surrounds the inner tube and has an inner diameter which is somewhat larger than the outer diameter of the inner tube. The distal end of the shaft comprises a flexible balloon portion which is sealed to the distal end of the inner tube and extends rearwards along the inner tube for short distance, where it is sealed to a more rigid shaft tubing. The balloon portion is capable of expansion when fluid under pressure is directed into the space between the shaft and the inner tube, while the rigid portion of the shaft is not.

After the balloon portion of the catheter is correctly positioned, as seen on the imaging screen, a fluid, such as a radiopaque contrast media under pressure, is introduced into the space between the inner tube and the shaft of the catheter so as to cause the balloon portion to expand and to press against the occluding matter on the inside of the blood vessel. The expansion of the balloon is carefully regulated to prevent possible over-expansion and over-stressing of the wall of the catheter which might cause it to rupture, while yet putting sufficient force on the blood vessel to accomplish the objectives of the procedure. When the desired enlargement of the occluded portion of the artery has been attained, pressure on the inside of the catheter is relieved, the balloon shrinks to its original size and is removed through the guide catheter. In some prior art catheters, lateral or axial shrinkage of the balloon which occurs at the time of deflation can result in undesirable curving of the distal end of the catheter.

In known catheter, for percutaneous transluminal angioplasty, the proximal end of the catheter comprises a mount which receives the proximal ends of the inner tube and of the shaft and seals them in spaced apart relationship, while providing a passageway for supplying fluid under pressure to the space therebetween. A spring within the mount exerts a force on the inner tube in the distal direction, relative to the mount. When the catheter is pressurized, the inner tube moves against the spring to accomodate the decrease in the length of the balloon which occurs when the balloon expands. Upon release of the pressure, the spring returns the inner tube to its distal position, and the diameter of the balloon is reduced to approximately its former diameter to ease removal of the catheter from the blood vessel. The possibility of curvature of the catheter and shift of position during inflation of the balloon are shortcomings of this device.

In catheters for coronary angioplasty a balloon of higher profile than the main shaft are currently in use.

Accordingly, there is a need for a catheter having a smooth profile and wherein the expanded balloon does not change position within the vessel site and which does not curl during inflation.

SUMMARY OF INVENTION

The catheter of the present invention is a coaxial catheter with a flexible inner tubing and an outer tubing of filament-reinforced elastomeric material. An inflatable balloon portion is formed at the distal end of the outer tubing and is anchored to the distal end of the inner tubing. The balloon and other portions of the outer tubing are reinforced by continuous helical filaments which repeatedly cross each other, being divided into segments which exhibit different behavior when the catheter is internally pressurized. Thus, the balloon portion of the shaft becomes shorter in length when under pressure, while a moving portion of the shaft becomes longer. By suitably balancing the lengths and the angle of the weave of the respective balloon and moving portions of the reinforcing filaments, the changes in length under pressure of these two portions of the shaft are made to offset each other. Thus, corrections in the position of the inner tubing relative to the outer tubing of the catheter are not needed and the balloon portion remains in the desired position in the blood vessel.

In the catheter of the invention, the reinforcing filaments in at least the balloon and the movable portions of the outer tubing take the form of a braid which is imbedded or otherwise encased in yielding plastic material. Prior to pressurization of the catheter, the filaments of the balloon portion lie at an angle which is less than a critical angle of 54.73°, relative to the axis of the balloon. The movable portion of the catheter shaft is constructed with a continuing weave of the same filaments, but these filaments lie at an angle which is greater than the critical angle, relative to the axis of the movable portion. The application of internal pressure to the catheter has opposite effects upon these two portions. Under increasing pressure, the diameter of the balloon portion increases until the angle of the filaments in the wall of the balloon reaches the critical angle and then stops. At the same time, the diameter of the movable portion of the outer tubing decreases until the angle of the filaments in the wall of the movable portion reach the critical angle. As the length of the balloon portion decreases, the length of the movable portion of the outer tubing increases and by proper selection of initial diameters and lengths of the two portions, the shortening of the balloon portion is offset. There is no tendency for the balloon to change position. In catheter of the invention, the proximal end of the inner tubing is fixed, relative to the outer tubing of the catheter. There is no need for an adjusting spring or for manipulation of the position of the inner tubing relative to that of the outer tubing.

Accordingly, it is an object of the invention to prove an improved balloon catheter for percutaneous transluminal coronary angioplasty.

It is an object of the present invention to provide a dilatation catheter for use in balloon angioplasty which can be used without risk of shifting of the location of the balloon from a desired position inside a blood vessel as a result of inflation of the catheter.

It is another object of the invention to provide a balloon catheter which does not require re-positioning of the inner tube relative to the shaft of the catheter during inflation.

It is still another object of the invention to provide a balloon catheter which is capable of operation, at body temperature, at pressures of up to 20 atmospheres.

It is a further object of the invention to provide a balloon catheter which has the outward appearance of tubing of a consistent diameter over its full length.

Still another object of the invention is to reduce the likelihood of kinking of a balloon catheter while in use, while preserving flexibility and the ability of the catheter to transmit force.

Still other objects and advantages of the invention will in part be obvious and will in part be apparent from the specification.

The invention accordingly comprises an article of manufacture possessing the features, the properties, and the relations of elements which will be exemplified in the article hereinafter described, and the scope of the invention will be indicated in the claims.

BRIEF DESCRIPTION OF THE DRAWINGS

For a fuller understanding of the invention, reference is had to the following description, taken in connection with the accompanying drawings in which.

DETAILED DESCRIPTION OF THE INVENTION

Figure 1:
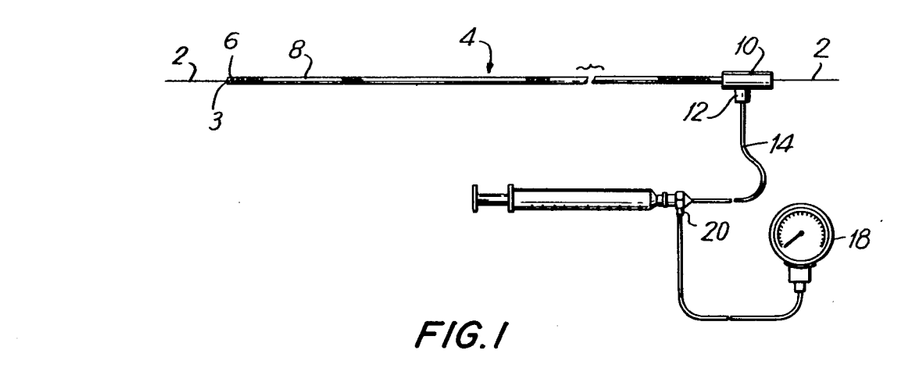
FIG. 1 is a plan view of a balloon catheter showing an attachment for supplying inflating fluid under pressure.

Reference is first made to FIG. 1 in which the location of a guide wire 2 and balloon catheter shaft 4 are shown. The guide wire 2 is, for example, about 0.015 inches in diameter and is shown, positioned in the inner passageway 3 of the catheter. The guide wire passes through tip 6 of the catheter, into balloon portion 8, through the remainder of shaft 4 of the catheter, and out through proximal catheter fitting 10. Attached to catheter fitting 10 by means of connecting tee 12 is pressure tubing 14 into which fluid can be forced by means of syringe 16 or other inflation device. Pressure in the fluid can be monitored by means of a gage 18 which is connected to pressure tubing 14 by means of a second connecting tee 20. The guide catheter which is also conventionally used in placing the balloon catheter in position in a blood vessel is not illustrated.

Figure 2A:
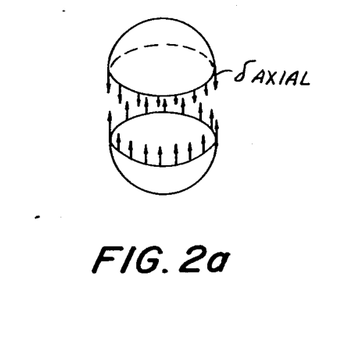
FIGS. 2(a) and 2(b) are schematic diagrams of the axial and circumferential stresses produced in the wall of a hollow cylindrical body by internal pressure.
Figure 2B:
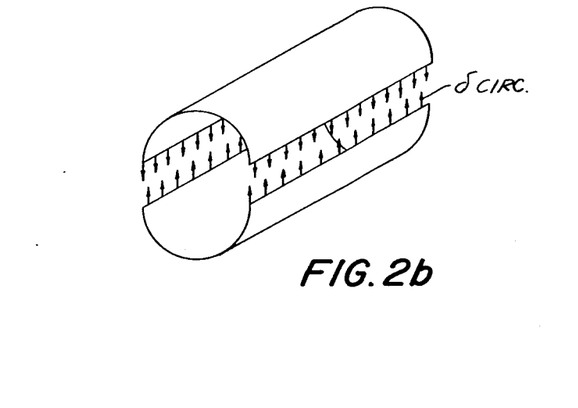

Reference is now made to FIG. 2 for an exposition of some of the physical principles upon which the invention relies. FIGS. 2(a) and 2(b) are respective schematic representations of the axial and circumferential stresses acting within the wall of a hollow cylindrical container which is pressurized internally in the same way as the balloon portion of a catheter axial stress axial is derived as follows:

$$\sigma_{axial} \times d \times \pi = \text{Area} \times \text{Pressure} = \frac{d^2 \times \pi}{4} \times P$$

where d is the diameter of the cylinder. Thus:

$$\sigma_{axial} = \frac{d \times P}{4}.$$

Similarly, the circumferential stress $\sigma_{circ}$ is found from the expression:

$\sigma_{circ} \times L \times 2 = \text{Area} \times \text{Pressure} = d \times L \times P$, where L equals length. Thus:

$$\sigma_{circ} = \frac{L \times P}{2}.$$

The angle of the resultant of the two forces can be expressed as:

$$\tan^2 = \frac{\sigma_{circ}}{\sigma_{axial}} = 2.$$

The angle, $\alpha$ of the resultant vector is thus:

$$\alpha = \tan^{-1}\sqrt{2} = 54.73°.$$

When, therefore, inelastic fibers lying in the plastic walls of a portion of the catheter are at an angle which is equal to the critical angle of 54.73°, relative to the axis, the system is at equilibrium and an increase in the internal pressure of the catheter will result in no change in the catheter diameter. As will be seen, this fact is utilized in the catheter of the invention to limit expansion of the balloon portion as well as to limit the reduction in diameter of a movable portion of the catheter shaft, enabling the accompanying changes in length of these parts under pressure to offset each other.

Figure 3A:
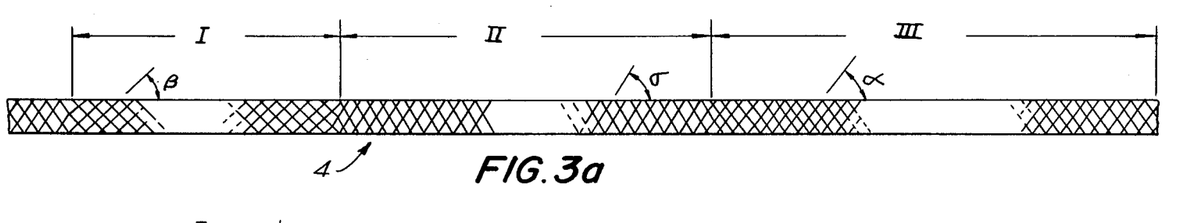
FIGS. 3(a) and 3(b) are schematic representations of the reinforcing braid of the invention in the depressurized and pressurized conditions, respectively.
Figure 3B:
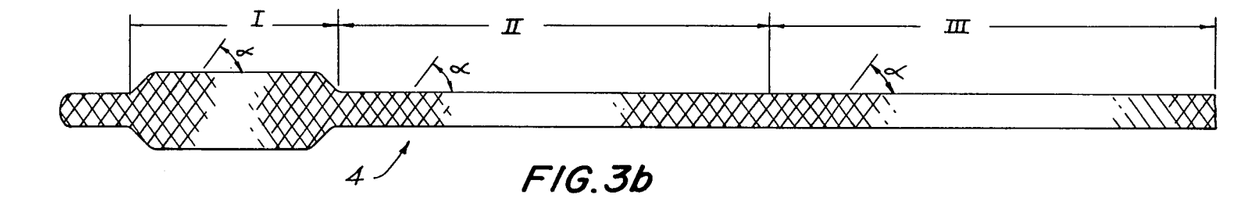

As indicated schematically in FIG. 3(a), the length of catheter shaft 4 of the invention is divided into three portions: a balloon portion I, a movable shaft portion II, and an immovable shaft portion III. FIG. 3(a) shows the orientation of the filaments in the various portions of the catheter shaft prior to the application of pressure to the inside of the catheter. FIG. 3(b) shows the orientation of the same filaments after the application of pressure.

Balloon portion I of the catheter is constructed using braided filaments or fibers lying in helices having an angle $\alpha$ relative to the axis which is less than the critical angle. When the balloon has been pressurized (FIG. 3(b)), the filaments lie in equilibrium at the critical angle and further expansion of the balloon does not occur. The helical filaments in movable portion II of the shaft lie initially at an angle which is greater than the critical angle. As pressure is increased, the shaft elongates until the filaments come to rest at the critical angle of 54.73°. Finally, in the immovable portion of the shaft, the filaments have an initial angle which is equal to the critical angle. The dimensions of immovable portion III do not change when the balloon is pressurized.

As shown in FIG. 3(b) after pressurizing, the filaments in each of the three portions of the catheter are all at the critical angle, e.g., 54.73°, relative to the axis of the system. It will be understood that in a preferred mode of construction the shaft includes continuous helical filaments or fibers of substantially inelastic material which are woven or braided into a reinforcing tube in which the filaments cross each other as they wind along the axis of the tube.

Figure 4A:
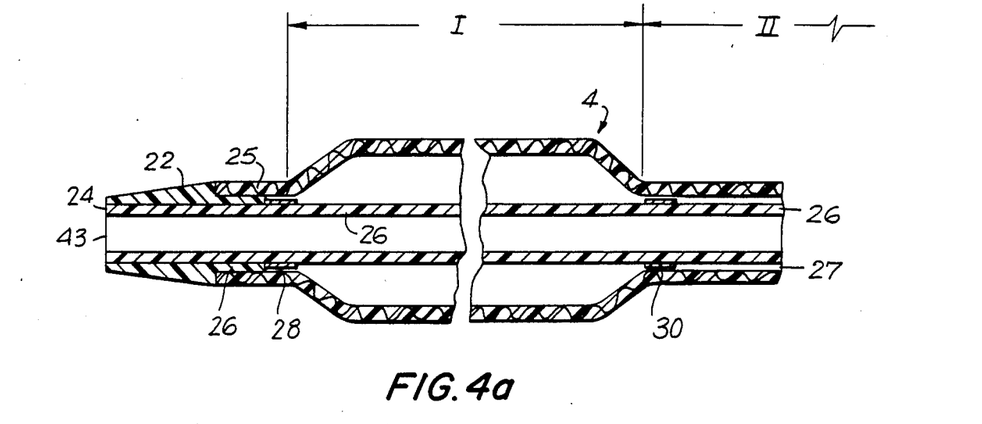
FIGS. 4(a), 4(b) and 4(c) are sectional views of the balloon portion, the shaft portions, and of the catheter fitting of the invention.
Figure 4B:
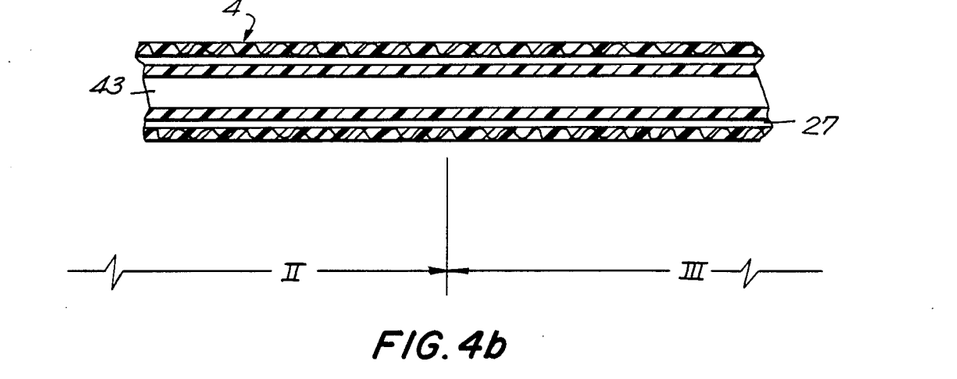
Figure 4C:
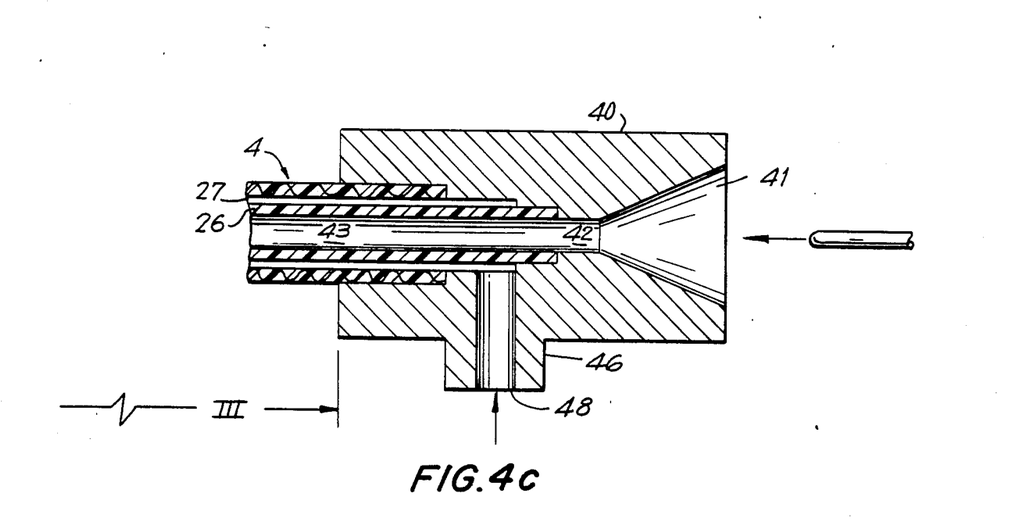

Details of the construction of a working balloon catheter in accordance with the invention are illustrated in the embodiment of FIGS. 4(a), 4(b) and 4(c), where FIG. 4(a) shows balloon portion I and the beginning of moving portion II of the shaft. FIG. 4(b) shows the other end of moving portion II and the beginning of immovable shaft portion III. Finally, FIG. 4(c) shows the proximal end of the catheter and illustrates the manner in which the shaft and the inner tube are supported in the connector to receive fluid under pressure.

The distal end 25 of catheter 4 of FIG. 4(a) has a tapered, hollow plastic tip 22 to which distal end 24 of inner catheter tube 26 is sealed. Inner tube 26 is made of a polytetrafluoroethylene plastic having an outside diameter of 0.72 mm. and an inside diameter of 0.50 mm. through which a guide wire having a diameter of about 0.015" may be passed. Neck 26 on distal tip 22 is sealed to the distal end of balloon portion I of shaft 4. As shown in FIG. 4(a) the balloon has been expanded by the application of pressure to the fluid space between the inner wall of the catheter shaft 4 and the outer surface of inner tube 26. The length of balloon portion I after inflation is 20 mm.; an other dimension, as is appropriate for the angioplasty to be performed, may of course, be used. The outside diameter of shaft portions II and III (and the unexpanded diameter of balloon portion I) is 1.33 mm., with an inside diameter of 1.00 mm. The expanded diameter of balloon portion I (illustrated in FIG. 4(a)) may range is from 2.5 mm. or less up to 10 mm. or more may be used, depending upon surgical requirements.

The different portions of the shaft include reinforcing continuous filaments of nylon lying at, respectively, angles of less than critical angle 54.73°, greater than the critical angle, and equal to the critical angle, in a polyurethane body. The polyurethane material may be applied to the filamentary material by dipping or coating the filaments which have been shaped into a tube about a mandrel. The unpressurized lengths of these portions were calculated in the manner to be discussed below.

Also shown in FIG. 4(a) are two bands 28, 30 of radio-opaque material, such as gold or platinum, which are placed around inner tube 26 to mark the ends of balloon portion I so that the balloon can be located radiographically in the blood vessel.

The proximal end of catheter 4 is fastened inside fitting 40 as shown in FIG. 4(c) so as to provide access to the space between inner tube 26 and shaft 5 by fluid under pressure. Fitting 40 includes a central opening 41 for a guide wire which is connected via central passageway 42 to central lumen 43 in inner tube 26 and thence to and out of tip 22.

Both immovable shaft portion III and inner catheter tube 26 are sealed into fitting 40 in spaced-apart, coaxial relationship. Access to the space between the outer surface of inner tube 26 and the inner surface of immovable shaft portion III is provided via passageway 48 in Luer connection 46 which extends laterally from catheter terminal block 40.

The catheter just described was found to be capable of operation at pressures of up to 20 atmospheres at a normal body temperature of 37° C. The catheter has the outward appearance of a uniform tubing, with a consistent diameter and has a smooth continuous surface over its full length. It has the lowest profile possible. The catheter does not require a spring as the catheter dip does not move back when balloon inflation occurs. The catheter has the further advantage that, in the event of rupture, the broken portions of the catheter are restrained by the filaments and cannot form an umbrella which would affect removal of the catheter from the patient. Since full length filaments are used in forming the fabric of the outer tubing, the likelihood of kinking of the catheter is reduced, while the catheter remains flexible and preserves its ability to transmit force. At the same time, friction produced during travel of the catheter on the guide wire is minimized.

When the balloon is inflated, movable portion II elongates while the balloon remains in the selected position as it is formed at the distal end of the inner tubing. Since the shaft of the balloon catheter lies in a guiding catheter, the full length of the shaft is available, if needed, to accommodate a change in length which offsets the decrease in length of the balloon portion due to expansion.

The following sets forth the relationship between the structural elements of the various portions of the catheter and provides a basis for calculating dimensions.

First, to find the inflated and deflated pitches of the filamentary spiral in a balloon so that the change in length of the balloon due to expansion can be calculated, it is assumed that the principle filamentary material of which the braid is made will comprise, for example, nylon which exhibits little stretching under tension.

Figure 5A:
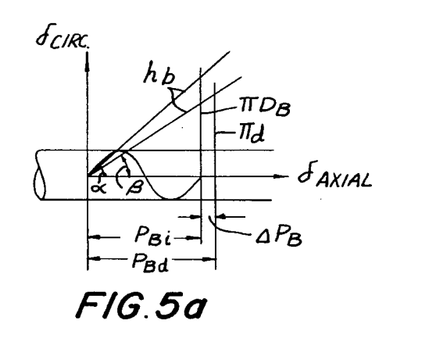
FIGS. 5(a) and 5(b) are schematic diagrams of the balloon and moving portions of the shaft which are useful in the explanation of further features of the invention.

As illustrated in FIG. 5, the pitch $P_{Bi}$ of the inflated balloon is given by:

$$P_{Bi} = \pi D_B / \tan \alpha,$$

where D is the inflated diameter of the balloon portion and $\alpha$ is the critical angle. At equilibrium, the hoop force radial and the axial forces axial results in the critical angle $\alpha$ given above, e.g., $\alpha = 54.73°$.

The pitch length $P_{Bd}$ of the deflated balloon is given by:

$$P_{Bd} = \pi d_B / \tan \beta,$$

where d is the main diameter of the deflated tube and $\beta$ is the angle of the filaments relative to the axis. Taking the length of the hypotenuse h as constant in the inflated and deflated condition of the balloon, the relationship between the inflated and deflated diameters is found;

$$h_B \sin \alpha = D_B$$

$$h_B \sin \beta = d_B$$

$$\sin \beta = (d_B \sin / D_B)$$

Since $\alpha = 54.73°$, sin $\alpha = 0.8165$, and: sin $\beta = 0.8165$ (d/D)

Thus, the angle $\beta$ of the filaments in the fabric is determined as a function of the critical angle and the inflated and deflated diameters of the balloon.

Figure 5B:
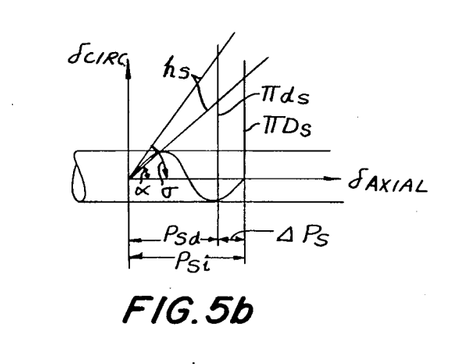

The same basic procedure is followed in the calculation of the parameters of the movable shaft, as illustrated in connection with 5(b).

$$h_s = \frac{D_s}{\sin\alpha} = \frac{d_s}{\sin\sigma}$$

where $h_s$ is the length of the hypotenuse, $D_s$ is the diameter of the inflated shaft, $d_s$ is the diameter of the deflated shaft, $\sigma$ is the angle of the weave in the deflated braid, and as before, $\alpha$ is the critical angle 54.73°.

The two pitch lengths are given by:

$$P_{sd} = \frac{D_s}{\tan\alpha}, P_{si} = \frac{d_s}{\tan\sigma}$$

where $P_{sd}$ is the pitch of the deflated shaft and $P_{si}$ is the pitch of the inflated shaft. The change in length per unit pitch is thus:

$$\Delta P_s = P_{si} - P_{sd}$$

The number $N_s$ of pitch units required to produce a required change in balloon length $L_B$ is:

$$N_S = \frac{\Delta L_B}{\Delta P_s}$$

and the total movable shaft length $L_s$ can be found:

$$L_s = N_S \times P_{sd}.$$

Since the change in length of the balloon from FIG. 5(a) is:

$$\Delta_B = L_{Bd} - L_{Bi},$$

the required pitch number in the movable shaft portion can be calculated. In the working example described above, the length of the catheter was 135 cm., the length of the balloon before pressurizing was about 30 mm. and the length of the moving portion of the catheter before pressurizing was approximately 265 mm.

Figure 6:
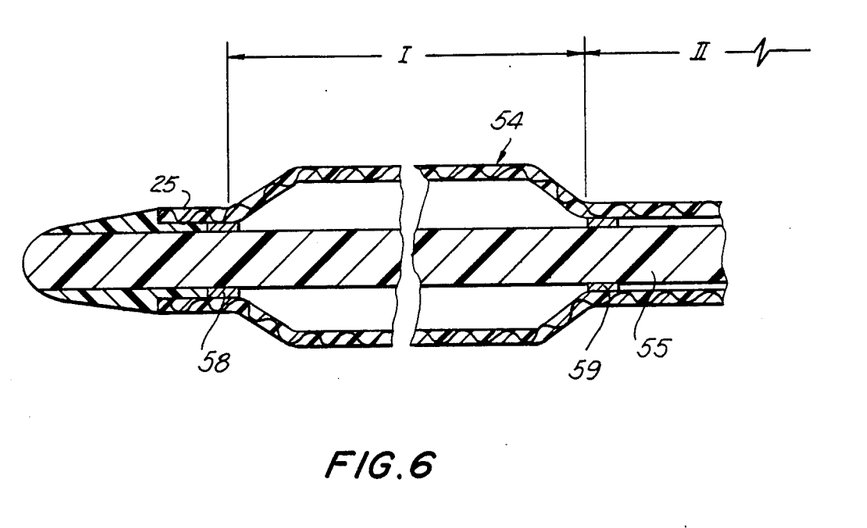
FIG. 6 is a sectional view of a catheter constructed in accordance with another embodiment of the invention with the proximal end of the balloon portion fixed to a guide wire.

In a balloon catheter, in accordance with another embodiment of the invention, a catheter includes a balloon portion I and a moving portion II having a distal end 25 as in the case of catheter 4 in FIG. 4a. In this embodiment, distal end 25 of the catheter is fixed to the distal end of a guide shaft.

Balloon portion I and moving portion II of the shaft of the catheter include reinforcing continuous filaments lying at, respectively, angles of less than critical angle 54.73° and greater than the critical angle. Thus, the catheter is formed in the same manner as catheter 4. The balloon catheter of FIG. 6 may include radial opaque markers as in catheter 4 of FIG. 4.

When using a catheter constructed in accordance with this embodiment of the invention, the balloon portion of the catheter is inserted into the vessel at the same time the guide wire is inserted. Thus, introduction of the balloon portion to the selected position is facilitated. Balloon portion I inflates and movable portion II elongates while the balloon remains in the selected position as described in connection with the earlier embodiment.

It will be understood that, to insure the delivery of ample fluid under pressure to the balloon portion of the shaft, it is necessary to limit the reduction in the cross-sectional area of the space between the shaft portion of the catheter and the inner tube so as to prevent shutting off the flow of fluid to the balloon portion.

As will be clear to those skilled in the art, the balloon catheter of the invention is capable of substantial variation in its physical dimensions as well as in its use. Also, the materials used in construction of the catheter may be varied from those use in the working example so long as the rules of biological compatibility are observed. Further, while the invention has been disclosed in the setting of a catheter surgical for use, it will be clear to those skilled in the art that the teachings of the invention have utility in other fields.

It will thus be seen that the objects set forth above, among those made apparent from the preceding description, are efficiently attained and, since certain changes may be made in the above article without departing from the spirit and scope of the invention, it is intended that all matters contained in the above description and shown in the accompanying drawings shall be interpreted as illustrative and not in a limiting sense.

It is also to be understood that the following claims are intended to cover all of the generic and specified features of the invention herein described and all statements of the scope of the invention which, as a matter of language, might be said to fall therebetween.

What is claimed is:

1. A dilatation catheter having a balloon portion which expands when the catheter is pressurized, the catheter comprising:

a shaft of elastomeric material having a longitudinal axis, said elastomeric material reinforced with filaments which lie at an angle relative to the axis of the shaft, including a movable portion and a balloon portion, the movable portion having filaments which lie at an angle which is greater than a predetermined critical angle relative to the axis of the shaft, the critical angle being the angle at which expansion of the shaft stops when pressurized internally, the movable portion increasing in length when the catheter is pressurized, the balloon portion of the shaft being capable when internally pressurized of expansion in diameter to provide a balloon, the filaments of the balloon portion lying at an angle which is less than the critical angle, whereby, when the balloon portion is expanded under pressure, expansion of the balloon stops when the filaments lie at the critical angle, the increase in length of the movable portion corresponding substantially to a decrease in length of the balloon portion when the catheter is pressurized so that the location of the balloon portion remains substantially at the position prior to expansion.

2. The dilatation catheter of claim 1 in which the shaft further comprises:

an immovable portion in which the filaments lie at the critical angle, the length of the immovable portion remaining constant when the catheter is pressurized.

3. The dilatation catheter of claim 2, in which the balloon portin is at the distal end of the shaft, the movable portion lies adjacent thereto, and the remainder of the shaft comprises the immovable portion.

4. The dilatation catheter of claim 2 in which the diameter of the unpressurized shaft is substantially uniform along the full length.

5. The dilatation catheter of claim 2 in which the shaft is formed of biologically compatible elastic coating means on the filaments of the balloon portion.

6. The dilatation cather of claim 5 in which the filaments comprise nylon.

7. The dilatation catheter of claim 2 in which the filaments of the shaft comprise a tubular braid.

8. The dilatation catheter of claim 2, wherein the filaments of the shaft comprise fibers lying in helicies.

9. The dilatation catheter of claim 1 in which the length of the balloon portion decreases when the catheter is pressurized and the resulting decrease in length is offset, at least in part, by an increase in length of the movable portion.

10. The dilatation catheter of claim 9 in which the decrease in length of the balloon portion of the catheter is offset by the increase in length of the movable portion of the catheter, whereby the position of the balloon portion does not change when the balloon is expanded.

11. The dilatation catheter of claim 1, in which the balloon portion is formed at the distal end of the shaft and the movable portion lies adjacent thereto.

12. The dilatation catheter of claim 1 further including:
inner tube means coaxially disposed inside the shaft, the inner tube means sealed to the distal end of the shaft to provide an annular space for receiving fluid under pressure between the shaft and the inner tube means.

13. The dilatation catheter of claim 12 further including:
connector means to which the inner tube means and the shaft are sealed, the connector maintaining the inner tube means and the shaft in coaxial relationship; and
passageway means in the connector means for passing fluid under pressure into the space between the inner tube means and the shaft.

14. The dilatation catheter of claim 12 in which the distal end of the balloon portion of the shaft is fixed to the distal end of the inner tube means.

15. The dilatation catheter of claim 12 in which the inner tube means comprises an elongated axial passageway for use in threading the catheter onto a guide wire.

16. The dilatation catheter of claim 12 in which the diameter of the unpressurized shaft is substantially uniform along the full length.

17. The dilitation catheter of claim 12 in which, when pressurized, the reduced diameter of the movable portion of the shaft remains greater than the diameter of the inner tube means so as to permit the passage of fluid under pressure into and out of the balloon portion.

18. The dilatation catheter of claim 12 in which the filaments comprise nylon, the inner tube means comprises polytetrafluoroethylene, and in which the filamentary material is embedded in polyeurethane.

19. The dilatation catheter of claim 1 in which the diameter of the unpressurized shaft is substantially uniform along the full length.

20. The dilatation catheter of claim 1 in which the shaft is formed of biologically compatible elastic coating means on the filaments of the balloon portion.

21. The dilatation catheter of claim 20 in which the filaments comprise nylon.

22. The dilatation catheter of claim 1 in which the filaments of the shaft comprise a tubular braid.

23. The dilatation catheter of claim 1, further including a guide wire disposed within the shaft with the distal end of the balloon portion fixed to the guide wire in the distal region thereof.

24. The dilatation catheter of claim 1, wherein the filaments of the shaft comprise fibers lying in helicies.

25. A balloon catheter assembly for introduction into a blood vessel, comprising:
an inner tube having a longitudinal axis;
an outer tube in coaxial relation to the inner tube;
the inner diameter of the outer tube being larger than the outer diameter of the inner tube so that the two tubes are axially displaceable with respect to each other and form an annular space between the tubes, and the distal end of the inner tube extending beyond the distal end of the outer tube with the distal end of the outer tube sealed to the inner tube;
the outer tube formed of an elastomeric material reinforced by filamentary material which lie at an angle relative to the axis of the tubes and having at least an inflatable balloon portion and and elongation portion;
the filamentary material in the balloon portion lying at an angle which is less than the critical angle relative to the axis, the critical angle being the angle at which expansion of the tubes stops when pressurized internally, so that when fluid is introduced under pressure into the annular space between the tubes, the balloon portions expands in diameter until the filamentary material is extended at the critical angle; and
the filamentary material in the elongation portion lying at an angle greater than the critical angle so that the elongation portion expands in length in response to the pressure of the fluid;
whereby a balloon forms with the increase in length of the elongation portion corresponding substantially to the decrease in length of the balloon portion when the catheter is pressurized so that the location of the balloon portion remains substantially at the position before expansion.

26. The dilatation catheter of claim 25, further including a guide wire disposed within the shaft with the distal end of the balloon portion fixed to the guide wire in the distal region thereof.

27. The dilatation catheter of claim 25, wherein the filaments of the shaft comprise fibers lying in helicies.

28. A balloon catheter assembly for introduction into a blood vessel, comprising:
a catheter guide wire having a distal end and a proximal end; and
a catheter shaft having a longitinal axis and a distal end and a proximal end, the shaft of an elastomeric material reinforced with filaments, and including a balloon portion and a movable portion; the balloon portion of the shaft being capable when internally pressurized of expansion in diameter to provide the balloon, the filaments of the balloon portion lying at an angle which is less than a predetermined critical angle relative to the axis, the critical angle being the angle at which expansion of the shaft stops when pressurized internally, whereby, when the balloon portion is expanded under pressure, expansion of the balloon stops when the filaments lie at the critical angle; the movable portion having filaments which lie at an angle which is greater than a predetermined critical angle relative to the axis of the shaft, the critical angle being the angle at which expansion of the shaft stops when pressurized internally, the movable portion increasing in length when the catheter is pressurized;

the wire disposed within the shaft with the distal end of the balloon portion fixed to the guide wire; the increase in length of the movable portion corresponding substantially to a decrease in length of the balloon portion when the catheter is pressurized so that the location of the balloon portion remains substantially at the position prior to expansion.

29. The balloon catheter of claim 28, wherein the shaft is fixed to the guide wire in the region of the distal end of the wire.

30. The dilatation catheter of claim 28, wherein the filaments of the shaft comprise fibers lying in helicies.

* * * * *